US008740970B2

(12) United States Patent  (10) Patent No.: US 8,740,970 B2
Hamman et al.  (45) Date of Patent: Jun. 3, 2014

(54) SYSTEM AND METHOD FOR ATTACHING A VESSEL IN A VASCULAR ENVIRONMENT

(75) Inventors: Baron L. Hamman, Dallas, TX (US); William E. Cohn, Bellaire, TX (US); Devin S. Dobie, Saint Paul, MN (US); Kirk S. Honour, Shorewood, MN (US); Dana Ray Mester, Oakdale, MN (US)

(73) Assignee: Castlewood Surgical, Inc., Dallas, TX (US)

(*) Notice: Subject to any disclaimer, the term of this patent is extended or adjusted under 35 U.S.C. 154(b) by 458 days.

(21) Appl. No.: 12/629,656

(22) Filed: Dec. 2, 2009

(65) Prior Publication Data

US 2011/0130624 A1  Jun. 2, 2011

(51) Int. Cl.
*A61F 2/06* (2013.01)
(52) U.S. Cl.
USPC .......................................... 623/1.23; 623/1.36
(58) Field of Classification Search
USPC ......... 606/108, 150, 153, 198, 149; 623/1.23, 623/1.36; 600/36
See application file for complete search history.

(56) References Cited

U.S. PATENT DOCUMENTS

| 4,222,380 A | 9/1980 | Terayama |
| 4,553,542 A | 11/1985 | Schenck et al. |
| 4,553,543 A | 11/1985 | Amarasinghe |
| 4,622,970 A * | 11/1986 | Wozniak ....................... 606/149 |
| 4,770,176 A | 9/1988 | McGreevy et al. |
| 4,827,940 A | 5/1989 | Mayer et al. |
| 4,836,596 A | 6/1989 | Owen |
| 4,911,164 A | 3/1990 | Roth |
| 5,042,161 A | 8/1991 | Hodge |
| 5,053,041 A | 10/1991 | Ansari et al. |
| 5,480,407 A | 1/1996 | Wan et al. |
| 5,542,937 A | 8/1996 | Chee et al. |
| 5,554,162 A | 9/1996 | DeLange |
| 5,643,254 A | 7/1997 | Scheldrup et al. |
| 5,669,905 A | 9/1997 | Scheldrup et al. |
| 5,868,763 A | 2/1999 | Spence et al. |

(Continued)

FOREIGN PATENT DOCUMENTS

| CN | 120630153 A | 8/2012 |
| JP | 2003532457 | 11/2003 |

(Continued)

OTHER PUBLICATIONS

R.K. Wolf, M.D., "Anastomotic Defices for Coronary Surgery," May 2004, 7 pages.

(Continued)

*Primary Examiner* — Dianne Dornbusch
*Assistant Examiner* — Robert Lynch
(74) *Attorney, Agent, or Firm* — Patent Capital Group (57) ABSTRACT

An apparatus is provided in one example embodiment and includes a body section having an upper surface, a lower surface, and an inner edge circumferentially arranged around at least a portion of an open area. The apparatus also includes a tool extending from the body section into the open area for holding a graft vessel. The lower surface of the body section opposes a receiving vessel when the tool is positioned to transfer the graft vessel to the receiving vessel, such that the graft vessel is axially accessible through the open area to be attached to the receiving vessel. In more specific embodiments, the body section has first and second opposing ends defining a gap sized to permit the vessel to pass through.

13 Claims, 10 Drawing Sheets

(56) References Cited

U.S. PATENT DOCUMENTS

| | | | |
|---|---|---|---|
| 5,904,697 A | 5/1999 | Gifford, III et al. | |
| 5,944,728 A | 8/1999 | Bates | |
| 6,019,722 A | 2/2000 | Spence et al. | |
| 6,030,370 A | 2/2000 | Kupka et al. | |
| 6,074,401 A | 6/2000 | Gardiner et al. | |
| 6,113,612 A | 9/2000 | Swanson et al. | |
| 6,149,658 A | 11/2000 | Gardiner et al. | |
| 6,165,186 A | 12/2000 | Fogarty et al. | |
| 6,193,734 B1 | 2/2001 | Bolduc et al. | |
| 6,206,827 B1 | 3/2001 | Chin et al. | |
| 6,224,619 B1 | 5/2001 | Hill | |
| 6,251,092 B1 | 6/2001 | Qin et al. | |
| 6,309,416 B1 | 10/2001 | Swanson et al. | |
| 6,352,543 B1 | 3/2002 | Cole | |
| 6,358,258 B1 | 3/2002 | Acia et al. | |
| 6,368,341 B1 | 4/2002 | Abrahamson | |
| 6,371,964 B1* | 4/2002 | Vargas et al. | 606/153 |
| 6,440,163 B1 | 8/2002 | Swanson et al. | |
| 6,508,822 B1 | 1/2003 | Peterson et al. | |
| 6,514,265 B2 | 2/2003 | Ho et al. | |
| 6,517,558 B2 | 2/2003 | Gittings et al. | |
| 6,533,812 B2 | 3/2003 | Swanson et al. | |
| 6,551,314 B1 | 4/2003 | Hill et al. | |
| 6,551,332 B1 | 4/2003 | Nguyen et al. | |
| 6,565,582 B2 | 5/2003 | Gifford, III et al. | |
| 6,575,985 B2 | 6/2003 | Knight et al. | |
| 6,605,104 B2 | 8/2003 | Sato et al. | |
| 6,607,541 B1 | 8/2003 | Gardiner et al. | |
| 6,613,059 B2 | 9/2003 | Schaller et al. | |
| 6,616,675 B1 | 9/2003 | Evard et al. | |
| 6,620,177 B2 | 9/2003 | Buelna et al. | |
| 6,635,214 B2 | 10/2003 | Rapacki et al. | |
| 6,641,593 B1 | 11/2003 | Schaller et al. | |
| 6,652,540 B1 | 11/2003 | Cole et al. | |
| 6,660,015 B1 | 12/2003 | Berg et al. | |
| 6,673,085 B1 | 1/2004 | Berg | |
| 6,695,859 B1 | 2/2004 | Golden et al. | |
| 6,699,256 B1 | 3/2004 | Logan et al. | |
| 6,699,257 B2 | 3/2004 | Gifford, III et al. | |
| 6,702,829 B2 | 3/2004 | Bachinski et al. | |
| 6,719,768 B1 | 4/2004 | Cole et al. | |
| 6,723,038 B1 | 4/2004 | Schroeder et al. | |
| 6,730,103 B2 | 5/2004 | Dakov | |
| 6,743,169 B1 | 6/2004 | Green et al. | |
| 6,743,170 B1 | 6/2004 | Spence et al. | |
| 6,802,847 B1 | 10/2004 | Carson et al. | |
| 6,802,848 B2 | 10/2004 | Anderson et al. | |
| 6,808,498 B2 | 10/2004 | Laroya et al. | |
| 6,814,743 B2 | 11/2004 | Chin et al. | |
| 6,960,217 B2 | 11/2005 | Bolduc | |
| 7,001,401 B1 | 2/2006 | Castañeda et al. | |
| 7,063,711 B1 | 6/2006 | Loshakove et al. | |
| 7,112,211 B2 | 9/2006 | Gifford, III et al. | |
| 7,122,040 B2 | 10/2006 | Hill et al. | |
| 7,150,742 B2 | 12/2006 | Takamoto et al. | |
| 7,212,870 B1 | 5/2007 | Helland | |
| 7,294,139 B1 | 11/2007 | Gengler | |
| 7,425,219 B2* | 9/2008 | Quadri | 623/1.35 |
| 7,763,037 B2 | 7/2010 | Hamman | |
| 7,776,062 B2 | 8/2010 | Besselink et al. | |
| 8,029,519 B2 | 10/2011 | Breton et al. | |
| 8,486,094 B2 | 7/2013 | Hamman | |
| 2001/0001826 A1 | 5/2001 | Bolduc et al. | |
| 2002/0022852 A1 | 2/2002 | Dakov | |
| 2002/0077636 A1 | 6/2002 | Arcia et al. | |
| 2003/0120291 A1 | 6/2003 | Chin et al. | |
| 2003/0125755 A1 | 7/2003 | Schaller et al. | |
| 2003/0176878 A1 | 9/2003 | Bolduc et al. | |
| 2003/0208214 A1 | 11/2003 | Loshakove et al. | |
| 2004/0068276 A1 | 4/2004 | Golden et al. | |
| 2004/0087985 A1 | 5/2004 | Loshakove et al. | |
| 2004/0127919 A1 | 7/2004 | Trout et al. | |
| 2005/0043749 A1 | 2/2005 | Breton et al. | |
| 2005/0070924 A1 | 3/2005 | Schaller et al. | |
| 2005/0267498 A1 | 12/2005 | Hendricksen et al. | |
| 2005/0277958 A1 | 12/2005 | Levinson | |
| 2006/0025788 A1 | 2/2006 | Loshakove et al. | |
| 2006/0212066 A1 | 9/2006 | Hamman | |
| 2008/0004640 A1 | 1/2008 | Ellingwood | |
| 2008/0027482 A1 | 1/2008 | Sekido et al. | |
| 2008/0177276 A1 | 7/2008 | Teague et al. | |
| 2008/0293996 A1 | 11/2008 | Evans et al. | |
| 2009/0005725 A1 | 1/2009 | Shorey | |
| 2009/0018555 A1 | 1/2009 | Hamman | |
| 2009/0054841 A1 | 2/2009 | Hamman | |
| 2009/0076454 A1 | 3/2009 | Hamman et al. | |
| 2009/0093825 A1 | 4/2009 | Logan | |
| 2009/0264835 A1 | 10/2009 | Schuermann | |
| 2009/0270908 A1 | 10/2009 | Tekulve et al. | |
| 2009/0287193 A1 | 11/2009 | Desai et al. | |
| 2010/0010533 A1 | 1/2010 | Burke et al. | |
| 2010/0010608 A1 | 1/2010 | Tockman et al. | |
| 2010/0057053 A1 | 3/2010 | Terashi et al. | |
| 2010/0185228 A1 | 7/2010 | Tekulve et al. | |
| 2010/0318065 A1 | 12/2010 | Miyata et al. | |
| 2010/0331954 A1 | 12/2010 | Sahatjian et al. | |
| 2011/0004238 A1 | 1/2011 | Palmer et al. | |
| 2011/0066159 A1 | 3/2011 | Teague et al. | |
| 2011/0082385 A1 | 4/2011 | Diaz et al. | |
| 2012/0271336 A1 | 10/2012 | Hamman et al. | |
| 2013/0267985 A1 | 10/2013 | Arai et al. | |

FOREIGN PATENT DOCUMENTS

| | | |
|---|---|---|
| JP | 2004167214 | 6/2004 |
| WO | WO 01/70119 A1 | 9/2001 |
| WO | WO 2011/068591 | 6/2011 |

OTHER PUBLICATIONS

Ernesto Tappainer, "New Device for Saphenous Vein-to-Aorta Proximal Anastomosis Without Side-Clamping," Journal of Cardiothoracic Surgery, Apr. 17, 2007, 31 pages.

Medtronic, "U-Clip™ Anastomotic Device and Spyder® Device," copyright Medtronic, Inc. 2007, http://www.medtronic.com/cardsurgery/products/uclip_spyder.html#, retrieved Oct. 30, 2009, 2 pages.

Novare Surgical, "Enclose® II Anastomosis Assist Device," copyright 2009 Novare Surgical Systems, Inc., http://www.novaresurgical.com/enclose2/enclose2device/, retrieved Oct. 30, 2009, 1 page.

MedGadget, "Heartstring III Proximal Seal System for CABG," Apr. 14, 2008, copyright 2004-2009 Medgadget LLC, http://medgadget.com/archives/2008/04/heartstring_iii-proximal_seal_system_for_cabg.html, retrieved Oct. 30, 2009, 6 pages.

USPTO Nonfinal Office Action dated Aug. 15, 2007 for U.S. Appl. No. 11/084,453, filed Mar. 18, 2005, 8 pages.

USPTO Final Office Action dated Jan. 10, 2008 for U.S. Appl. No. 11/084,453 filed Mar. 18, 2005, 7 pages.

USPTO Nonfinal Office Action dated Apr. 22, 2008 for U.S. Appl. No. 11/084,453, filed Mar. 18, 2005, 9 pages.

Notification of Transmittal of the International Search REport and the Written Opinion of the International Searching Authority, or the Declaration (1 page), International Search Report (6 pages), and Written Opinion (8 pages) for International Application No. PCT/US2010/052253 mailed Jan. 26, 2011.

Request for Continued Examination and Amendment in U.S. Appl. No. 11/842,541, filed Jul. 14, 2011.

Non-Final Office Action in U.S. Appl. No. 12/273,484 mailed on Apr. 15, 2011.

Response to Non-Final Office Action dated Apr. 15, 2011 in U.S. Appl. No. 12/273,484, filed Jul. 14, 2011.

Final Office Action in U.S. Appl. No. 12/332,058 mailed on Jun. 16, 2011.

USPTO Oct. 17, 2007 Response to Aug. 15, 2007 Nonfinal Office Action from U.S. Appl. No. 11/084,453.

USPTO Feb. 21, 2008 RCE Response to Jan. 10, 2008 Final Office Action from U.S. Appl. No. 11/084,453.

USPTO Jun. 10, 2008 Response to Apr. 22, 2008 Nonfinal Office Action from U.S. Appl. No. 11/084,453.

(56) References Cited

OTHER PUBLICATIONS

USPTO Sep. 2, 2008 Final Office Action from U.S. Appl. No. 11/084,453.
USPTO Sep. 22, 2008 RCE Response to Sep. 2, 2008 Final Office Action from U.S. Appl. No. 11/084,453.
USPTO Dec. 9, 2008 Nonfinal Office Action from U.S. Appl. No. 11/084,453.
USPTO Dec. 22, 2008 Response to Dec. 9, 2008 Nonfinal Office Action from U.S. Appl. No. 11/084,453.
USPTO Mar. 16, 2009 Final Office Action from U.S. Appl. No. 11/084,453.
USPTO Mar. 27, 2009 RCE Response to Mar. 16, 2009 Final Office Action from U.S. Appl. No. 11/084,453.
USPTO Jun. 17, 2009 Nonfinal Office Action from U.S. Appl. No. 11/084,453.
USPTO Sep. 17, 2009 Response to Jun. 17, 2009 Nonfinal Office Action from U.S. Appl. No. 11/084,453.
USPTO Jan. 7, 2010 Final Office Action from U.S. Appl. No. 11/084,453.
USPTO Mar. 9, 2010 Appeal Brief Office Action from U.S. Appl. No. 11/084,453.
USPTO Jun. 2, 2010 Notice of Allowance from U.S. Appl. No. 11/084,453.
USPTO Nov. 9, 2010 Nonfinal Office Action from No. 11/842,541.
USPTO Jan. 14, 2011 Nonfinal Office Action from U.S. Appl. No. 12/332,058.
USPTO Feb. 3, 2011 Response to Nov. 9, 2010 Nonfinal Office Action from U.S. Appl. No. 11/842,541.
USPTO Apr. 14, 2011 Final Office Action from U.S. Appl. No. 11/842,541.
USPTO Apr. 14, 2011 Response to Jan. 14, 2011 Nonfinal Office Action from U.S. Appl. No. 12/332,058.
USPTO Apr. 15, 2011 Nonfinal Office Action from U.S. Appl. No. Nov. 18, 2008.
Response to Non-Final Office Action dated Jan. 14, 2013 in U.S. Appl. No. 12/235,469, filed Apr. 15, 2013.
Non-Final Office Action in U.S. Appl. No. 12/276,484 mailed on Mar. 29, 2013.
U.S. Appl. No. 13/851,903, filed Mar. 27, 2013 and entitled "System and Method for a Multi-Head Cutter in a Vascular Environment", Inventors, Kirk S. Honour et al.
U.S. Appl. No. 13/851,943, filed Mar. 27, 2013 and entitled "System and Method for a Multi-Head Cutter in a Vascular Environment", Inventors, Kirk S. Honour et al.
Non-Final Office Action in U.S. Appl. No. 12/235,469 mailed on Sep. 29, 2011.
Response to Non-Final Office Action dated Sep. 29, 2011 in U.S. Appl. No. 12/235,469, filed Dec. 20, 2011.
Supplemental Response and Amendment in U.S. Appl. No. 12/235,469, filed Jan. 3, 2012.
Final Office Action in U.S. Appl. No. 12/235,469 mailed on Jan. 26, 2012.
Request for Continued Examination and Amendment in U.S. Appl. No. 12/235,469, filed Apr. 26, 2012.
Non-Final Office Action in U.S. Appl. No. 12/235,469 mailed on Jan. 14, 2013.
Notice of Allowance in U.S. Appl. No. 11/842,541 mailed on Mar. 14, 2013.
Response to Non-Final Office Action dated Apr. 15, 2011 in U.S. Appl. No. 12/273,484, filed Jul. 15, 2011.
Final Office Action in U.S. Appl. No. 12/273,484 mailed on Oct. 21, 2011.
Request for Continued Examination and Amendment in U.S. Appl. No. 12/273,484, filed Jan. 23, 2012.
Request for Continued Examination and Amendment in U.S. Appl. No. 11/332,058, filed Sep. 16, 2011.
U.S. Appl. No. 13/359,437, filed Jan. 26, 2012, entitled "System and Method for Attaching a Vessel in a Vascular Environment", inventors William E. Cohn et al.
U.S. Appl. No. 13/358,700, filed Jan. 26, 2012, entitled "System and Method for Loading a Graft Vessel on a Vessel Holding Device for Delivery in a Vascular Environment," inventor Kirk S. Honour.
Final Office Action in U.S. Appl. No. 12/273,484 mailed on Oct. 11, 2013.
Non-Final Office Action in U.S. Appl. No. 13/359,437 mailed on Jul. 18, 2013.
Response to Non-Final Office Action dated Jul. 18, 2013 in U.S. Appl. No. 13/359,437, filed Oct. 18, 2013.
Final Office Action in U.S. Appl. No. 13/359,437 mailed on Dec. 10, 2013.
Japan Patent Office First Notice of Reasons for Refusal in Japanese Patent Application Serial No. JP 2012-542006 mailed on Oct. 17, 2013.
International Preliminary Report on Patentability and Written Opinion issued in PCT Application Serial No. PCT/US2010/052253 mailed on Jun. 14, 2012.
Notice of Allowance in U.S. Appl. No. 12/235,469 mailed on May 7, 2013.
Response to Non-Final Office Action in U.S. Appl. No. 12/273,484, filed Jul. 1, 2013.
Request for Continued Examination and Amendment in U.S. Appl. No. 12/332,058, filed Sep. 16, 2011.
Non-Final Office Action in U.S. Appl. No. 13/358,700 mailed on Nov. 21, 2013.
U.S. Appl. No. 13/621,205 entitled "System and Method for Providing an Elongated Coil Guide in a Vascular Environment" inventor(s) Kirk S. Honour et al., filed Sep. 15, 2012.
Non-Final Office Action in U.S. Appl. No. 13/621,205 mailed on Nov. 15, 2013.
Response to Restriction Requirement in U.S. Appl. No. 13/541,290, filed Jan. 14, 2014.
AF Response to Final Office Action dated Oct. 11, 2013 in U.S. Appl. No. 12/273,484, filed Dec. 11, 2013.
Notice of Allowance in U.S. Appl. No. 12/273,484 mailed on Dec. 26, 2013.
Non-Final Office Action in U.S. Appl. No. 12/332,058 mailed on Dec. 20, 2013.
Restriction Requirement in U.S. Appl. No. 13/541,290 mailed on Jan. 6, 2014.

\* cited by examiner

SYSTEM AND METHOD FOR ATTACHING A VESSEL IN A VASCULAR ENVIRONMENT

TECHNICAL FIELD

This disclosure relates in general to the field of cardiac and vascular surgery and, more particularly, to a system and method for attaching a vessel in a vascular environment.

BACKGROUND

In recent decades, the treatment of vascular diseases has grown exponentially in terms of sophistication and diversity. Most cardio-thoracic procedures, bypasses, and valve surgeries are routine, almost commonplace. Their popularity is due, in part, to their tremendous success rates and their ability to offer extraordinary benefits to a patient. Other types of surgeries have achieved a similar level of acceptance and popularity.

Many such procedures involve the use of medical devices, which have experienced considerable notoriety in recent years. Although these devices can automate and improve various types of procedures, many of these instruments suffer from a number of significant drawbacks. For example, the environment in which a surgeon performs such procedures is typically localized and, therefore, the size and shape of the medical devices used in such procedures is constrained by the environment. While a medical device may initially be advantageous in delivering tissue, vessels, or other devices to a surgical site, once deployed, the size or shape of the medical device often presents difficulties to surgeons trying to access the site. This detracts from the value of the surgery, adds unnecessary risk for a patient, and forces a surgeon to exercise extraordinary diligence in using such devices. Therefore, optimizing or simplifying any of these problematic issues may yield a significant reduction in risk for a patient and, further, minimize the accompanying burden for a surgeon.

DETAILED DESCRIPTION OF EXAMPLE EMBODIMENTS

Overview

An apparatus is provided in one example embodiment including a body section having an upper surface, a lower surface, and an inner edge circumferentially arranged around at least a portion of an open area. The apparatus further includes a tool extending from the body section into the open area for holding a graft vessel. The lower surface of the body section opposes a receiving vessel when the tool is positioned to transfer the graft vessel to the receiving vessel, such that the graft vessel is axially accessible through the open area to be attached to the receiving vessel. In more specific embodiments, the body section of the apparatus further includes a first end opposing a second end such that the first and second ends define a gap sized to permit the graft vessel to pass through. In other more specific embodiments the tool is axially spaced from the upper surface of the body section. In even more specific embodiments, the body section of the apparatus further includes a base and a cam operably connected to the base and adapted to move relative to the base. In this embodiment, the cam is configured to engage a portion of the tool to cause the tool to extend from the body section during movement of the cam in one direction and retract toward the body section during movement of the cam in an opposite direction. The movement of the cam may be a rotational movement.

Example Embodiments

To provide a more complete understanding of the present disclosure and features and advantages thereof, reference is made to the accompanying figures in which like reference numerals reference like parts. Where alternative embodiments are shown, common elements are similarly numbered and not separately described, with the addition of apostrophes to distinguish the embodiments.

Figure 1:
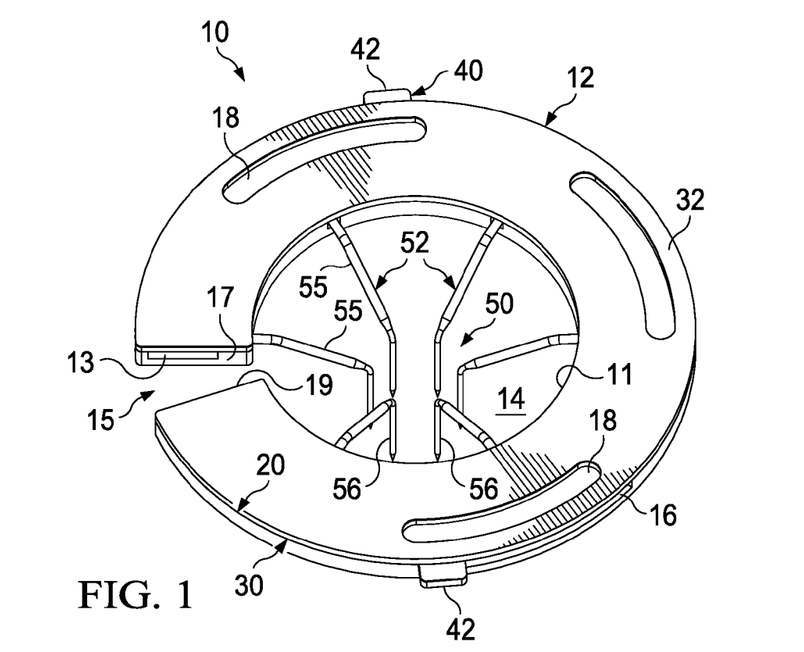
FIG. 1 is a top and side perspective view of one embodiment of a vessel holding device in an expanded position in accordance with the present disclosure.

FIG. 1 illustrates one embodiment of a vessel holding device 10 that may be used in cardiovascular bypass surgery. Vessel holding device 10 may include a body section 12 having a base 20, a top 30 with an upper surface 32, and a cam 40. Base 20 and top 30 may be joined together to form cavity 13 with cam 40 being movably seated between base 20 and top 30. Cavity 13 may be formed along an entire length of body section 12, from a first end 17 to a second end 19. Body section 12 may also include an inner edge 11 circumferentially arranged around at least a portion of open area 14, with a gap 15 defined between first and second ends 17 and 19. In one embodiment, open area 14 is coaxially aligned with body section 12. Vessel holding device 10 also includes a tool 50 for holding a graft vessel, in which tool 50 may extend from body section 12 into open area 14 and may be angled down below body section 12.

In example embodiments, vessel holding device 10 is capable of holding a graft vessel on tool 50 such that a surgeon may more easily perform suturing or other desired attachment methods to connect the graft vessel to a receiving vessel (e.g., an aorta). In addition, vessel holding device 10 is configured to allow the surgeon to choose the order in which the ends of the graft vessel are attached during a bypass procedure.

For purposes of teaching and discussion, it is important to understand the environment in which vessel holding device 10 may be used. The following foundational information may be viewed as a basis from which the present disclosure may be properly explained. Such information is offered earnestly, for purposes of explanation only and, accordingly, should not be construed in any way to limit the broad scope of the present disclosure and its potential applications and embodiments.

A coronary artery bypass graft (CABG) is a complex, yet common surgery to restore healthy coronary artery circulation to a patient. The procedure involves multiple steps and different techniques may be used (e.g., on-pump vs. off-pump bypass protocols). On-pump CABG is performed on a patient after the heart is stopped. A heart-lung machine removes all the blood from the body, oxygenates it, and returns it to the patient's body after the procedure is completed. Although on-pump procedures are common, they can have serious complications, including blood clots that can lead to a stroke, heart attack, or kidney failure. Off-pump coronary artery bypass (OPCAB) is an alternative technique in which the bypass is performed on a beating heart without the need for aortic clamping or cannulation, which may lessen any potential complications. However, in OPCAB surgery, the surgeon must create the anastomoses in such a way that blood loss is minimized for the safety of the patient and for the ability of the surgeon to perform the grafting or other attachment without having blood spewing from the opening in the aorta or artery.

The CABG procedure is often accomplished using a healthy graft vessel (e.g., vein or artery) from another part of the patient's body to reroute blood flow around a blockage in a targeted coronary artery. For example, a saphenous vein found in the leg is an often used vessel in CABG procedures. In addition, a radial artery located deep within the forearm may also be used. Alternatively, some surgeons utilize artificial vessels made from various synthetic materials (e.g., ePTFE, Dacron®, Gortex®) when, for example, the patient's other veins and arteries not suitable for use in bypass surgery. This may occur when the other veins are unhealthy or not sufficiently sized to be beneficial.

In a typical CABG patient, once a graft vessel is chosen from another part of the patient's body, surgery is performed to remove it. The graft vessel is then prepared for bypass surgery. Such preparation may include, for example, washing and cutting the graft vessel into desired segment lengths. Once a segment of the graft vessel has been prepared, one end of it is typically grafted near the base of the aorta (i.e., proximal anastomosis) and the other end is typically grafted distal to a blockage in a targeted coronary artery (i.e., distal anastomosis).

Many of the current devices and processes used in bypass procedures present difficulties for surgeons. For example, when the graft vessel is attached between the aorta and the targeted coronary artery, it is common for surgeons to create the proximal anastomosis at the aorta, before creating the distal anastomosis at the targeted coronary artery. However, it is often desirable to create the distal anastomosis before the proximal anastomosis. This is not always possible, though, because many vessel holding devices have an elongated configuration making it cumbersome, if not impossible, to safely load the graft vessel onto the device after one end of the graft vessel has already been attached to the targeted artery. Thus, even if creating the distal anastomosis prior to the proximal anastomosis is desirable, it is not always feasible due to the limitations of the current vessel holding device configurations.

The size and configuration of some vessel holding devices also present difficulties for the many surgeons who prefer hand suturing when attaching the ends of the graft vessel to an artery or aorta. Hand suturing can be difficult because it is time-consuming and requires considerable skills, including steady hands and dexterity to manipulate the components being used in the suturing process. The procedure can be made even more complicated if the component devices used to deliver the graft vessels prevent direct access to the surgical site or obstruct the view of the surgical site. Also, any attachment mechanism, including hand suturing, could become more difficult if the vessel holding device protrudes from the surgical site and requires steady, angled support from the surgeon or assistant during the suturing process. Therefore, it is desirable for the component devices to be configured and sized so as not to hinder or obstruct the surgeon's view and access to the surgical site, and to minimize handling required by the surgeon and assistant.

Yet another problem with many vessel holding devices occurs because the vessel holding devices disturb the inside of the aorta. When using the advantageous off-pump technique, many devices include mechanisms that are inserted into the aorta in order to minimize the flow of blood to the surgical site. Such devices may actually touch an inner wall of the aorta, which can cause debris or plaque to dislodge and travel through the blood vessels to various organs, causing substantial risk to the patient. Such a situation could potentially cause, for example, aortic damage, stroke, or even death for the patient. In addition, some devices also require a translational motion to be applied to the vessel holding device, which can increase the risk of damage to the aorta if the motion is not applied with the appropriate force.

Vessel holding device 10 as shown in FIGS. 1-8 overcomes many of these problems and provides a solution for surgeons who perform bypass procedures. Its unique design allows surgeons to more easily perform suturing or other procedures to attach an end of a graft vessel to a receiving vessel (e.g., an aorta). Procedures such as hand suturing may be performed through open area 14 of vessel holding device 10, which offers an unobstructed view and access to the surgical site when attaching the graft vessel to the receiving vessel. Also, the particular configuration of vessel holding device 10 responds to a rotational motion and permits the surgeon or assistant to more easily maintain vessel holding device 10 stationary relative to the surgical site. In addition, vessel holding device 10 minimizes contact with the inner wall of the aorta.

Vessel holding device 10, as described in the present disclosure, is also useful to surgeons for creating the distal anastomosis prior to the proximal anastomosis. That is, the distal end of a graft vessel may be attached to one receiving vessel (e.g., a coronary artery) prior to the proximal end being attached to another receiving vessel (e.g., an aorta). Once the distal end is attached to the distal receiving vessel, the proximal end of the graft vessel may be easily loaded onto vessel holding device 10. The compact size and configuration of vessel holding device 10 helps prevent interference with the distal anastomosis and permits easier placement of device 10 at the proximal anastomosis surgical site.

Turning to the particular features of the example embodiment of vessel holding device 10, shown in FIG. 1, tool 50 may include a plurality of arms 52, partially disposed within body section 12, which extend from body section 12 into open area 14 and angle down below body section 12. Arms 52 may also include tips 56 provided at distal ends of arms 52, where tips 56 are positioned in substantially vertical alignment relative to body section 12. Arms 52 may also include angled segments 55 connected to upper ends of tips 56 and extending from upper ends of tips 56 radially outward toward base 20. In one embodiment, angled segments 55 may be sufficiently angled from base 20 to provide an axial spacing between a substantially flat lower surface 28 of base 20 and upper ends of tips 56 (more easily seen in FIGS. 8B, 8C, 8D, & 8F). In one embodiment the axial spacing between lower surface 28 of base 20 and upper ends of tips 56 is approximately 0.09"-0.10". Lower surface 28 may be at least substantially parallel to upper surface 32 in one embodiment, and angled segments 55 could also provide an axial spacing from upper surface 32. Although one embodiment of tool 50 is shown and described herein having a portion axially spaced below lower surface 28, it will be appreciated that alternative configurations of tool 50 may not have any portions axially spaced below lower surface 28.

A lower end of tips 56 may be configured to be pointed and sufficiently sharp to pierce and hold a graft vessel being used in a cardiovascular procedure. Tips 56 are also sized to permit natural, rapid closure of holes created by tips 56 once tips 56 are removed from the graft vessel. Another example vein-holding apparatus using sharp, pointed tips is provided by commonly assigned and co-pending U.S. patent application having Ser. No. 11/084,453 and entitled: System and Method For Attaching a Vein, an Artery, or a Tube in a Vascular Environment, filed Mar. 18, 2005, which is hereby incorporated by reference herein in its entirety.

FIG. 1 shows arms 52 of tool 50 in a fully expanded position. In one embodiment of vessel holding device 10, six tips 56 of arms 52 could form a maximum circular area approximately 8 mm in diameter. Typical harvested veins or other graft vessels have an approximate range size of 4-8 mm in diameter. Vessel holding device 10, however, could be made to accommodate virtually any diameter size. Although six arms 52 are shown in the embodiment of FIG. 1, vessel holding device 10 could be modified to accommodate any number of arms for holding a graft vessel during vascular surgery. Furthermore, it is within the broad teachings of this disclosure, that tool 50 could be configured in any number of alternative embodiments in which a graft vessel could be properly maneuvered and manipulated by device 10 as taught in this disclosure.

Gap 15 may be sized to permit a graft vessel to pass through when arms 52 are in the fully expanded position as shown in FIG. 1. In one embodiment, gap 15 has an increasing dimension from a narrowest section adjacent an inner circumference of body section 12 to a broadest section adjacent an outer circumference of body section 12. By way of example, gap 15 may have a dimension of 0.140" at its narrowest section. It will be appreciated that graft vessels are inherently supple and floppy and may be maneuvered through gap 15 even if the narrowest gap dimension is somewhat smaller than the graft vessel dimension. In this situation, the increasing dimension of gap 15 will assist the surgeon in manipulating the graft vessel to pass through gap 15.

Also shown in FIG. 1 are vertically-oriented elongated openings 18 disposed in top 30 that may be aligned with horizontally-oriented elongated openings 16 disposed between top 30 and base 20. In one embodiment, handles 42 of cam 40 may be slidably positioned in horizontally-oriented elongated openings 16 such that application of a rotating force to handles 42 thereby rotates cam 40 within cavity 13, causing arms 52 to extend and retract depending on which way the rotating force is applied. One embodiment permits arms 52 to retract toward the fully expanded position as shown in FIG. 1 when handles 42 are rotated in a clockwise direction. Conversely, in this embodiment, arms 52 may extend toward a fully converged position when handles 42 are rotated in a counterclockwise direction, as will be further shown and described herein.

Body section 12 of vessel holding device 10 may be formed of any suitable material including, molded pieces made of ABS/Polycarbonate blend or Acetal (Delrin). Other suitable materials may include, by way of example, polyvinyl chloride (i.e., PVC). The individual components, including base 20, top 30, and cam 40, may be formed through any acceptable method such as, for example, injection molding, or laser, mechanical, or chemical milling. In one embodiment, arms 52 are formed of nickel titanium (i.e., Nitinol), because of its superelastic property. Nitinol has an extraordinary ability to accommodate large strains and recover its original shape. In addition, it is compatible with the human body and therefore, widely used in medical devices. Arms 52 made of Nitinol may be manufactured using any customary process. One example includes a centerless grinding process to achieve stepped diameters as well as pointed lower ends of tips 56. Arms 52 may then be formed by thermal shape setting using cold-worked material, which may include the use of shaping tools and heat treatment. Once arms 52 are suitably formed, electropolishing may be applied to arms 52 in order to reduce friction when arms 52 extend and retract. In one embodiment, however, electropolishing may not be applied to at least a portion of tips 56 as a rougher surface finish of tips 56 may be desirable. A rougher surface finish of tips 56 may help prevent a graft vessel from slipping off tips 56 once the graft vessel is loaded onto tips 56 during a procedure. The rougher surface finish of tips 56 may also help maintain friction between tips 56 and a receiving vessel, such as an aorta, to help secure vessel holding device 10 at a surgical site during a procedure.

Figure 2:
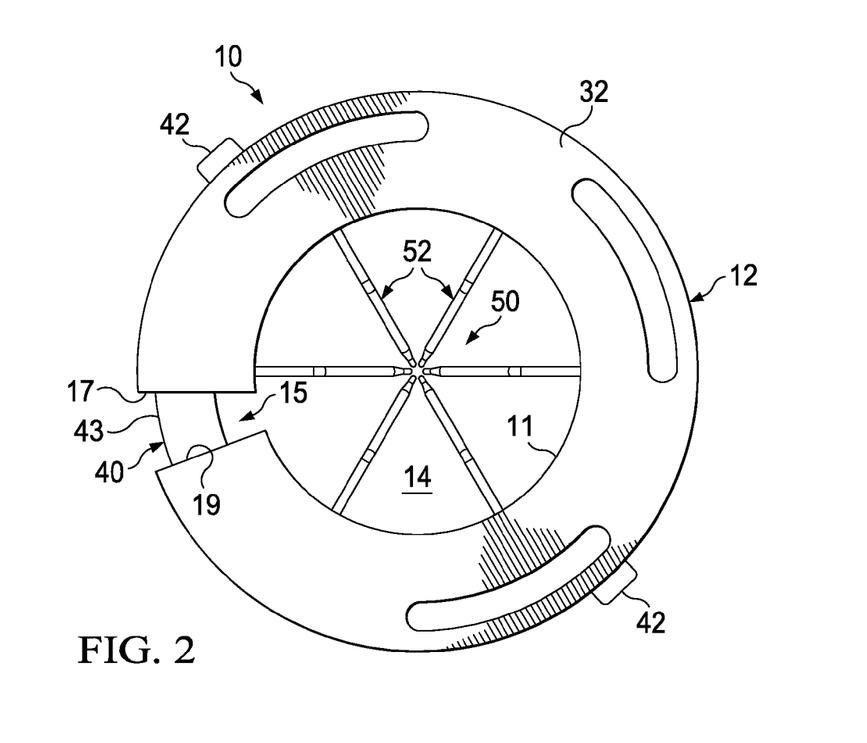
FIG. 2 is a top plan view of the embodiment of vessel holding device of FIG. 1 in a converged position in accordance with the present disclosure.

FIG. 2 illustrates a top plan view of vessel holding device 10 of FIG. 1 with arms 52 shown in the fully converged position. In one embodiment, a diameter of a circular area defined by arms 52 in the fully converged position is approximately 0.095". However, vessel holding device 10 can be configured to accommodate a smaller or larger diameter, as necessary, in the fully converged position. Body section 12 is sized to permit a surgeon to attach a graft vessel to a receiving vessel through open area 14. Generally, it is desirable for an outer diameter and thickness of body section 12 to be as small as functionally possible, while maintaining a diameter of inner edge 11 of body section to be sufficiently large to permit a surgeon to manipulate a graft vessel within open area 14. By way of example, in one embodiment, body section 12 may have an inner diameter (inner edge 11) of 1.0", an outer diameter of 1.78", and a vertical dimension of 0.14". In other example embodiments, the inner diameter may be at least 0.75" and the outer diameter may be at most 2.0." As will be appreciated, body section 12 could be configured with any alternative dimensions providing that a surgeon is able to maneuver and manipulate a graft vessel through open area 14 and to operate vessel holding device 10 in accordance with the present disclosure.

As shown in FIG. 2, cam 40 may include ring 43, which is rotatable within cavity 13. In one embodiment, when cam 40 is rotated counterclockwise, ring 43 advances across gap 15 from one opening of cavity 13, aligned with first end 17 of body section 12, to an opposite opening of cavity 13, aligned with second end 19 of body section 12. It will be appreciated that ring 43 may alternatively be configured to at least partially enter cavity 13 through the opposite opening or to only partially advance across gap 15. As shown in FIGS. 1 and 2, in one embodiment, arms 52 retract toward the fully expanded position when cam 40 is rotated in a clockwise motion and extend toward a fully converged position when cam 40 is rotated in a counterclockwise motion. Alternatively, vessel holding device 10 may be configured such that retraction and extension of arms 52 correspond to a counterclockwise motion and a clockwise motion, respectively. It will be appreciated that in such an alternative configuration, ring 43 of cam 40 may be designed to advance across gap 15 in a clockwise direction when arms 52 are extending toward a fully converged position.

Figure 3:
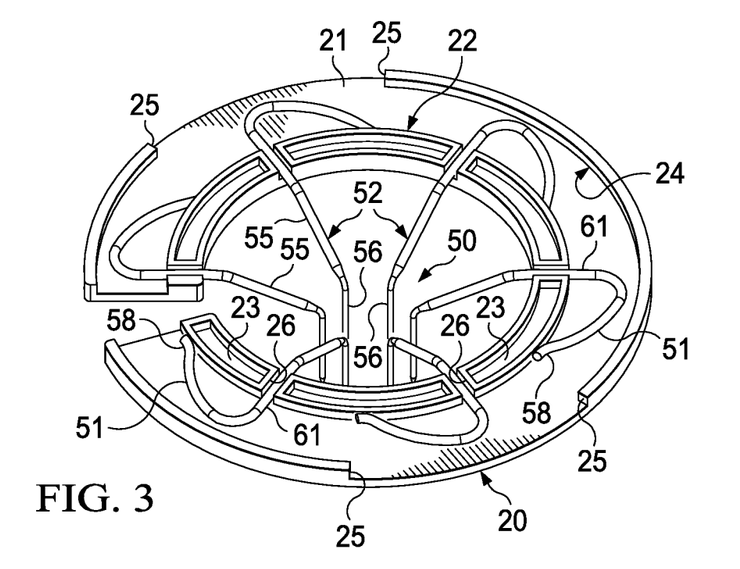
FIG. 3 is a top and side perspective view of one embodiment of a base and arms of vessel holding device of FIG. 1 in accordance with the present disclosure.

In FIG. 3, one embodiment of base 20 with arms 52 in a fully expanded position is shown. Base 20 may include an upwardly facing surface 21 disposed between an inner edge wall 22 and an outer edge wall 24. Outer edge wall 24 may be configured with a plurality of stops 25 such that a spacing is defined between each pair of opposing stops 25. As shown in the embodiment of FIG. 3, two spacings are defined between four stops 25 in outer edge wall 24. In alternative embodiments, however, outer edge wall 24 may be configured with fewer or greater stops defining fewer or greater spacings. Inner edge wall 22 may be aligned with inner circumference of base 20, and may be adapted to receive arms 52 through transverse slots 26. In one embodiment, transverse slots 26 may be symmetrically spaced around inner edge wall 22. A plurality of upwardly facing channels 23 may be formed in inner edge wall 22 and separated by transverse slots 26. In an example embodiment, each arm 52 may include a proximal portion 51 with a tail 58 slidably disposed against inner edge wall 22, where proximal portion 51 is configured generally to include an arcuate segment and a bend. Each arm 52 may also include a straight segment 61 connected to angled segment 55 and proximal portion 51, such that straight segment 61 is slidingly disposed through one transverse slot 26.

Figure 4:
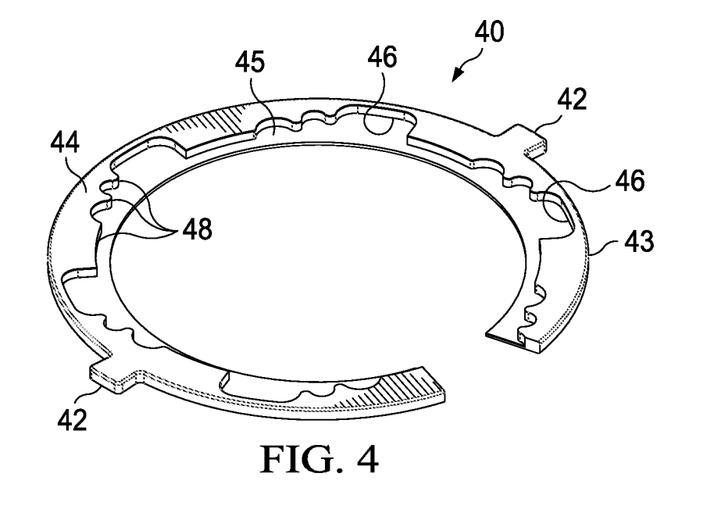
FIG. 4 is a bottom and side perspective view of one embodiment of a cam of vessel holding device of FIG. 1 in accordance with the present disclosure.
Figure 5:
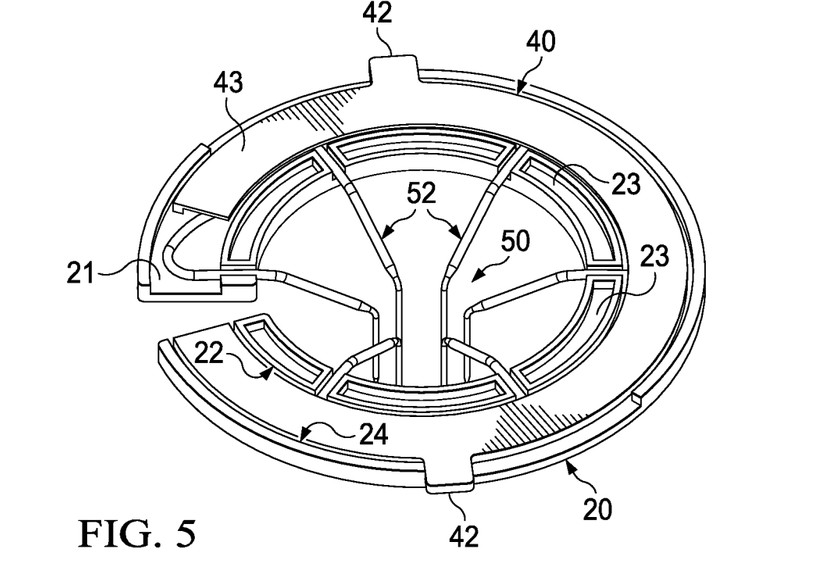
FIG. 5 is a top and side perspective view of the base of FIG. 3 with the cam of FIG. 4 seated therein in accordance with the present disclosure.

FIG. 4 is a bottom perspective view of one embodiment of cam 40 and FIG. 5 illustrates one arrangement of seating cam 40 in base 20. With reference to FIG. 4, a bottom surface 44 of ring 43 may provide a contoured depression 45 with a plurality of recessed parts 46, where each recessed part 46 could define a dimension in contoured depression 45 to accommodate one proximal portion 51 of one arm 52 in an original shape when arms 52 are in the fully expanded position. Adjacent to recessed parts 46 are a plurality of graduated contact surfaces 48 providing decreasing radial dimensions in contoured depression 45. As seen in FIG. 5, in one embodiment ring 43 of cam 40 may be seated between inner and outer edge walls 22 and 24 of base 20, such that contoured depression 45 opposes proximal arm portions 51 and at least a portion of upwardly facing surface 21 of base 20 opposes bottom surface 44 of ring 43. In one embodiment, contoured depression 45 and bottom surface 44 of cam 40 may slidably contact proximal arm portions 51 and upwardly facing surface 21, respectively.

The inner geometry of cam 40 may be configured to drive proximal arm portions 51 toward the center as cam 40 is rotated in a particular direction. In one embodiment shown in FIG. 4, the geometry of graduated contact surfaces 48 may be configured to engage proximal arm portions 51 as cam 40 is rotated in a counterclockwise direction, thereby applying a force to proximal arm portions 51. As the force is applied, proximal arm portions 51 are depressed causing straight segments 61 to slide radially inward through transverse slots 26 as arms 52 extend toward the fully converged position (shown in FIG. 2), and causing tails 58 to slide in a clockwise direction along inner edge wall 22. Once the counterclockwise rotation is completed, arms 52 are arranged in the fully converged position. In one embodiment, the geometry of contact surfaces 48 may be designed to help prevent the superelastic properties of arms 52 from inducing a clockwise rotational force on cam 40 when arms 52 are in the fully converged position. For example, when arms 52 are in the fully converged position, each of the contact surfaces 48 defining the smallest radial dimension and having an elongated surface area may engage one proximal arm portion 51. As cam 40 is rotated back in a clockwise direction, the geometry of contact surfaces 48 permits proximal arm portions 51 to gradually return to their original shape, causing straight segments 61 to slide radially outward through transverse slots 26 as arms 52 retract toward the fully expanded position, and causing tails 58 to slide in a counterclockwise direction along inner edge wall 22. During the clockwise rotation, the geometry of contact surfaces 48 may allow arms 52 to aid the rotation due to the superelastic properties of proximal portions 51 inducing a clockwise rotational force on cam 40. Once the clockwise rotation is completed, arms 52 are in the fully expanded position, with proximal arm portions 51 having recovered their original shapes and being disposed proximate recessed parts 46.

Contact surfaces 48 may be configured with curves and spacing to minimize a total surface area engaging and dragging along proximal arm portions 51. In one embodiment of cam 40, shown in FIG. 4, contact surfaces 48 are configured such that no more than two contact surfaces 48 engage any proximal arm portion 51 at any given time during rotation of cam 40. Such a configuration may further minimize frictional forces against proximal arm portions 51 and thereby increase the ease with which cam 40 may be rotated.

A lubricant, such as, for example, polydimethylisiloxane (i.e., pdms) may be used on any parts of vessel holding device 10 movably contacting other parts. For example, pdms may assist the sliding motion of proximal arm portions 51 and straight segments 61 with respect to cam 40 and base 20. Pdms may also reduce friction between base 20 and cam 40 and between top 30 and cam 40 when cam 40 is rotated. Such a lubricant could improve the ease with which cam 40 is rotated and arms 52 spring back to the fully expanded position. Proximal arm portions 51 may also be fitted with a sleeve (not shown) made of any suitable material, such as, polytetrafluoroethylene (i.e., PTFE), a shrink tubing material. In this configuration, a tube of the material being used may be fitted over proximal arm portion 51. Once heated, the tube would shrink and cling tightly to at least a part of proximal arm portion 51. Similar to a lubricant, this type of sleeve may assist the sliding motion of proximal arm portions 51 when cam 40 is rotated.

Figure 6:
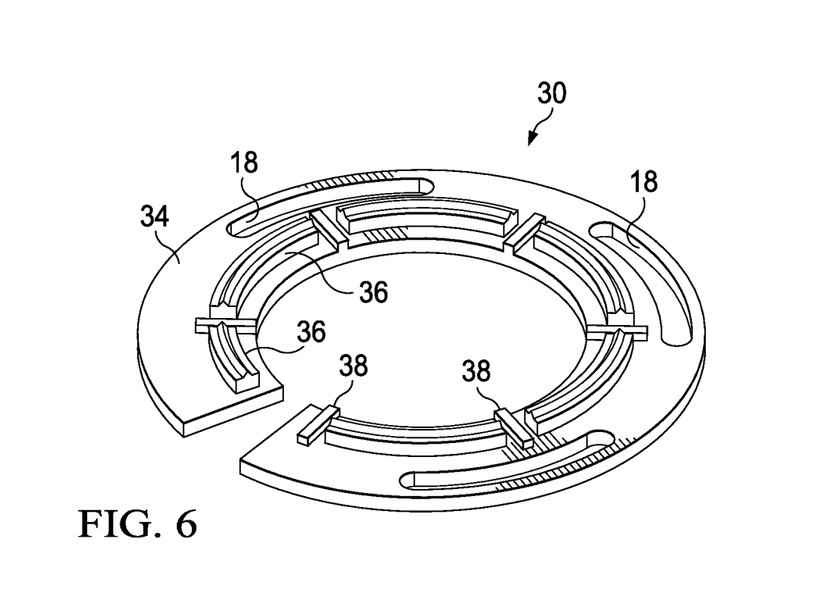
FIG. 6 is a bottom and side perspective view of one embodiment of a top of vessel holding device of FIG. 1 in accordance with the present disclosure.

With reference to FIG. 6, one embodiment of top 30 is illustrated. A bottom surface 34 of top 30 may be configured with a plurality of circumferential projections 36 adapted to be received by upwardly facing channels 23 of base 20 when top 30 and base 20 are connected. A plurality of transverse projections 38 may be spaced between circumferential projections 36 and adapted to enclose transverse slots 26 to permit controlled extending and retracting movement of arms 52 through transverse slots 26. Base 20 and top 30 may be joined together, with cam 40 rotatably seated between them, by an ultrasonic welding process, in accordance with one embodiment of the present disclosure. However, any acceptable manner of attachment may be used, and inner and outer edge walls 22 and 24 of base 20 the corresponding bottom surface 34 of top 30 may be configured in a variety of ways depending on how base 20 and top 30 are connected. For example, in an alternative embodiment, base 20 and top 30 may be joined together with appropriate hardware (e.g., nuts, bolts, screws). In yet another example embodiment, base 20 and top 30 may be formed with plastic portions that are snap-fitted together.

Figure 7A:
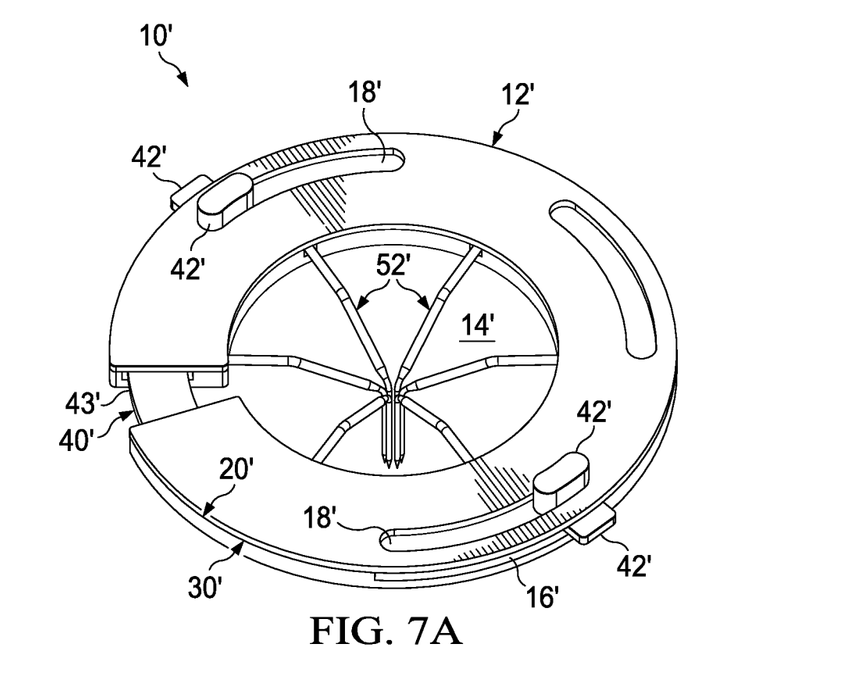
FIG. 7A is a top and side perspective view of another embodiment of the vessel holding device in accordance with the present disclosure.
Figure 7B:
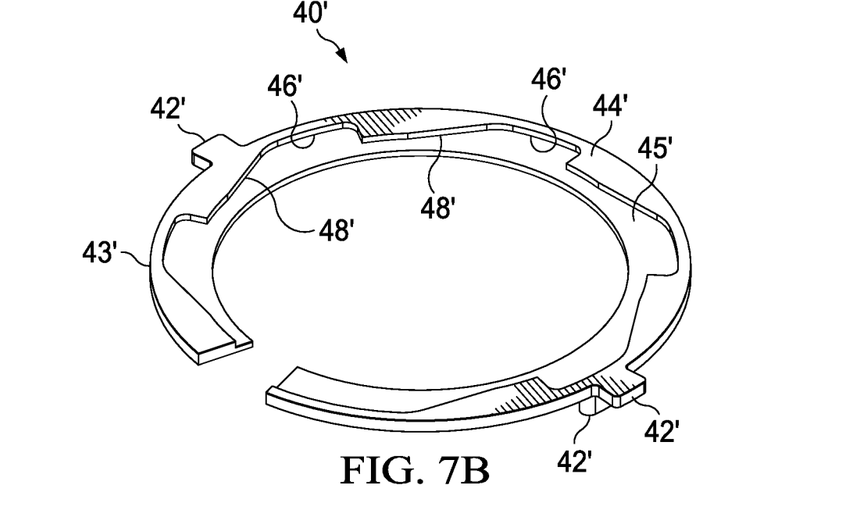
FIG. 7B is a bottom and side perspective view of another embodiment of a cam of vessel holding device of FIG. 7A in accordance with the present disclosure.

FIGS. 7A and 7B illustrate an alternative embodiment of vessel holding device 10' having an alternative cam 40'. With reference to FIG. 7A, L-shaped handles 42' are provided on cam 40'. L-Shaped handles 42' extend through vertically-oriented elongated openings 18' and through horizontally-oriented elongated openings 16'. It is within the broad teachings of this disclosure, however, for cam 40' to be provided with any configuration that permits its rotation relative to base 20'. With reference to FIG. 7B, an alternative bottom surface 44' of a ring 43' and a contoured depression 45' are shown. In alternative cam 40', recessed parts 46' may be similarly configured to recessed parts 46 of cam 40. However, contact surfaces 48' could alternatively be formed as angled surfaces that provide a single elongated surface for engaging each proximal arm portion (not shown, but configured in a similar manner to proximal arm portions 51 of FIG. 3) as cam 40' is rotated. It is within the broad teachings of this disclosure that cam 40' may be configured in any alternative embodiment such that proximal arm portions are maneuvered to cause arms 52' to retract and extend as a rotational forces are applied to cam 40'.

Figure 8A:
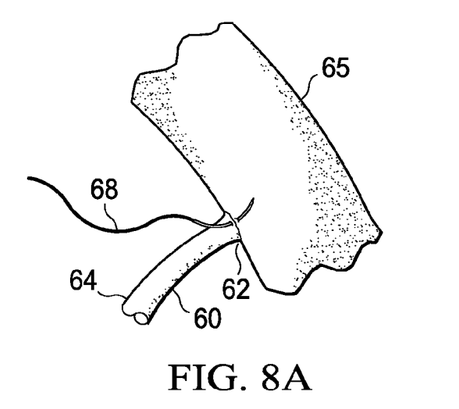
FIG. 8A is a side view showing a graft vessel being sutured to a distal receiving vessel in one example operation in accordance with the present disclosure.

FIGS. 8A through 8F illustrate an example off-pump CABG surgery in which a distal anastomosis is created before a proximal anastomosis. With reference to FIG. 8A, a schematic view showing the distal anastomosis in which a distal end 62 of a graft vessel 60 is being hand sutured with a suturing device 68 to a distal receiving vessel 65 (e.g., a coronary artery). The hand suturing may be performed using any type of suitable medical apparatus. For example, nitinol clips, retractors, or forceps, among others, may be used to assist the surgeon in suturing graft vessel 60 to distal receiving vessel 65. Also, while hand suturing is a commonly known and widely used technique for performing vascular grafts, any other appropriate methods may be used (e.g., biological glue, laser generated solder). Finally, while this example operation shows distal receiving vessel 65 being sutured first, it is within the broad teachings of this disclosure that vessel holding device 10 may be used to facilitate proximal and distal anastomoses in any order selected by the surgeon. Thus, in another example operation, the surgeon may create the proximal anastomosis before the distal anastomosis.

Figure 8B:
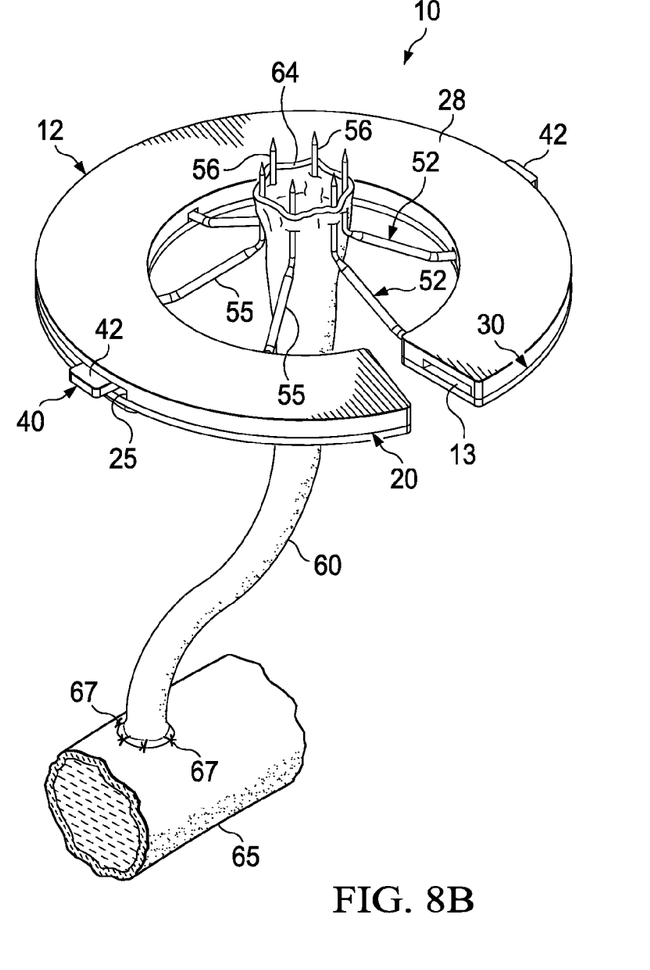
FIG. 8B is a bottom and side perspective view of a one embodiment of vessel holding device in an expanded position with the graft vessel of FIG. 8A attached thereto in accordance with one example operation in the present disclosure.

In FIG. 8B, the distal anastomosis is shown completed with sutures 67, and a proximal end 64 of graft vessel 60 is loaded onto tips 56 of vessel holding device 10. Any suitable means for loading graft vessel 60 onto tips 56 may be employed. In one example method, the surgeon and an assistant may load graft vessel 60 onto tips 56 of vessel holding device 10 using a pair of surgeon's pickups. While the assistant holds device 10, the surgeon manually loads proximal end 64 of graft vessel 60 over each tip 56 using pickups. Graft vessel 60 is then gently moved toward upper ends of tips 56. Other example methods of loading a graft vessel onto a vein-holding apparatus are shown in U.S. pending patent application Ser. No. 11/084,453, entitled: System and Method For Attaching a Vein, an Artery, or a Tube in a Vascular Environment, which was previously incorporated by reference herein in its entirety.

Figure 8C:
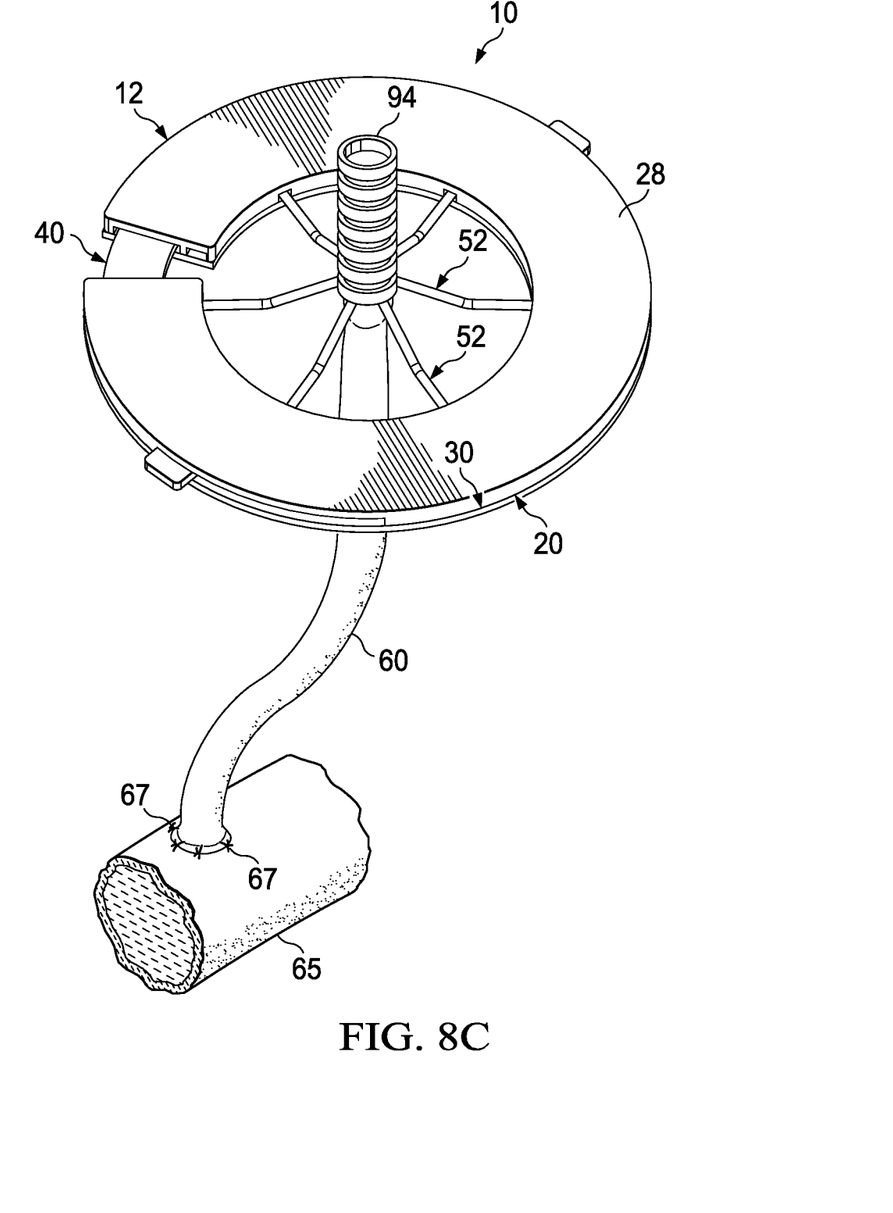
FIG. 8C is a bottom and side perspective view of the vessel holding device holding graft vessel of FIG. 8B in a converged position, including a coil element in accordance with one example operation in the present disclosure.

With reference to FIG. 8C, in one example surgery using vessel device 10, a coil element 94 may be applied to tips 56, such as any of coil elements disclosed in commonly assigned and co-pending U.S. patent application Ser. No. 12/332,058, entitled: System and Method For Providing a Coil Element in a Vascular Environment filed Dec. 10, 2008, which is hereby incorporated by reference herein in its entirety. Coil element 94 may be used to facilitate entry of tips 56 into an aortotomy of a receiving vessel and may be removed after tips 56 are suitably placed within the aortotomy. When coil element 94 is applied to tips 56, cam 40 may be rotated back in a clockwise direction such that coil element 94 alone prevents expansion of arms 52. Thus, retraction of arms 52 may occur as coil element 94 is removed, thereby removing the restraining force holding arms 52 in a converged position and allowing arms 52 to spring back into an expanded position. Alternatively, an obturator, as disclosed in the same co-pending U.S. patent application Ser. No. 12/332,058, could be used with vessel holding device 10 to facilitate entry of tips 56 into an aortotomy. For ease of illustration, and because its operation is more extensively described and shown in U.S. patent application Ser. No. 12/332,058, coil element 94 is not further shown.

Figure 8D:
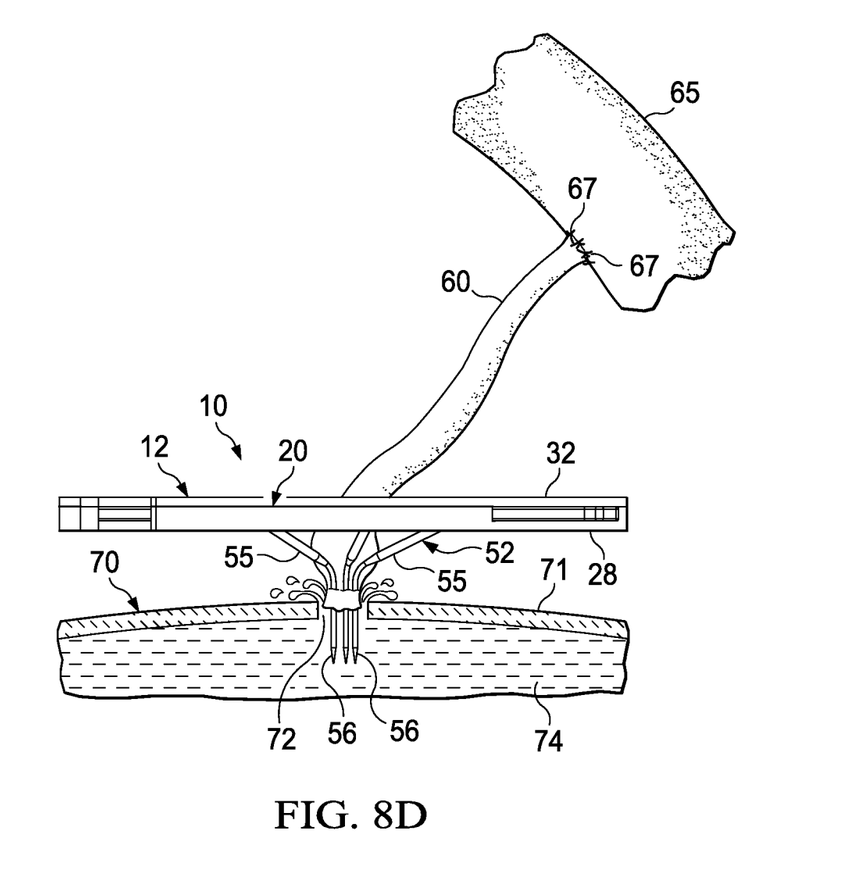
FIG. 8D is a side elevation view of the vessel holding device and graft vessel of FIG. 8C (without the coil element) inserted in a proximal receiving vessel shown in cross section in accordance with one example operation in the present disclosure.

After graft vessel 60 is loaded onto tips 56, a hole 72 (e.g., an aortotomy), shown in FIG. 8D, is cut in a proximal receiving vessel 70 (e.g., an aorta) through a vessel wall 71 (e.g., adventitia) using any suitable tools and procedures. The process shown in U.S. pending patent application Ser. No. 12/332,058 is one method that may be used in accordance with this disclosure. However, other appropriate hole cutting tools and procedures, both mechanical and automatic, are within the broad teachings of this disclosure to prepare a hole in proximal receiving vessel 70 for vessel holding device 10. Once hole 72 is cut, blood 74 may begin to flow out. The surgeon or assistant can prevent blood flow from hole 72 by putting a finger or other suitable device over hole 72, as disclosed in U.S. pending patent application Ser. No. 12/332,058, until device 10 is positioned in hole 72.

Figure 8E:
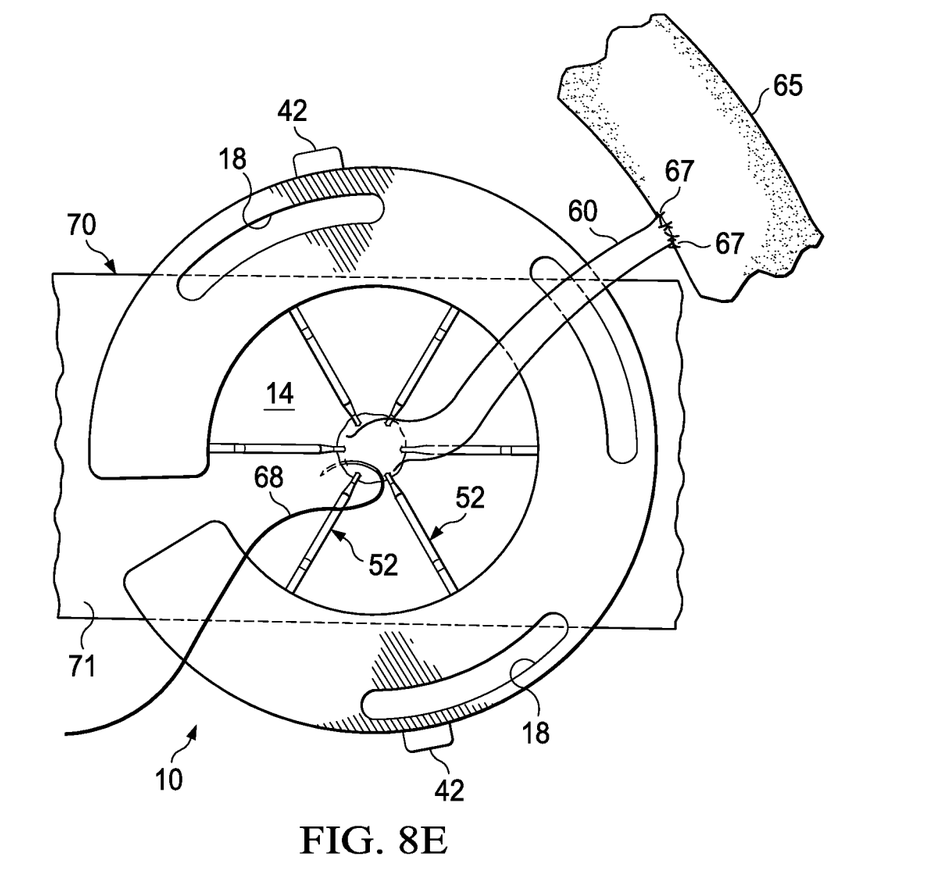
FIG. 8E is a top plan view of FIG. 8D with the vessel holding device in an expanded position and showing how a proximal end of the graft vessel may be sutured to the receiving vessel in accordance with one example operation in the present disclosure.
Figure 8F:
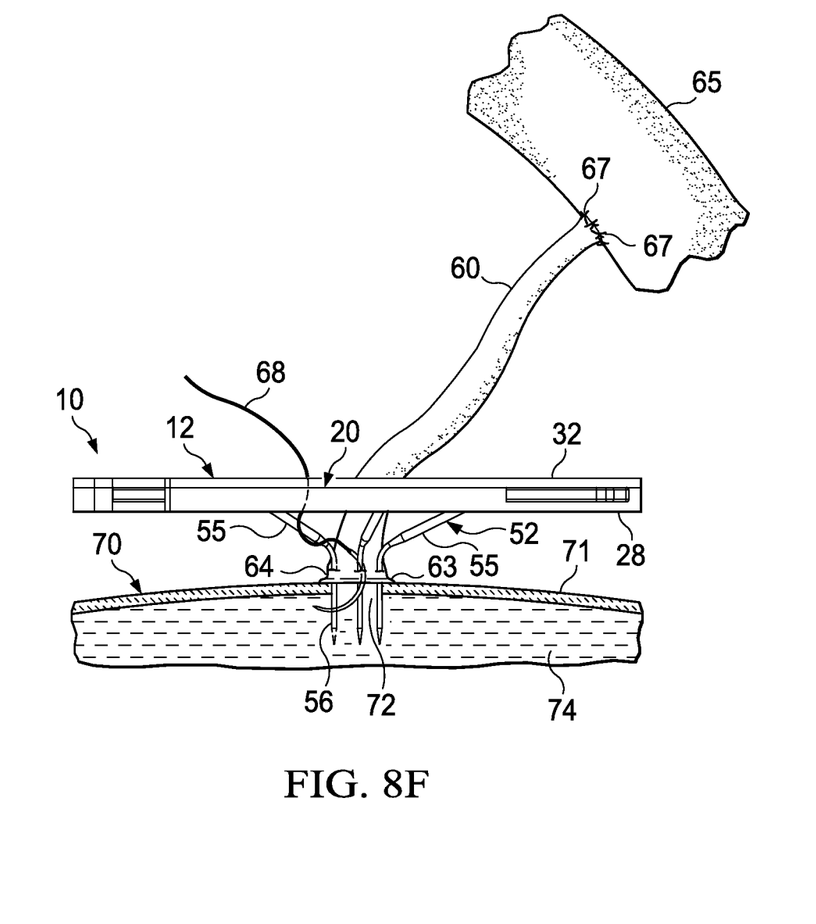
FIG. 8F is a side elevation view of FIG. 8E.

FIGS. 8D through 8F illustrate a transfer operation in which vessel holding device 10 delivers graft vessel 60 to fill the void in proximal receiving vessel 70. FIG. 8D illustrates how hole 72 is plugged with vessel holding device 10 and loaded graft vessel 60. Upon entry of tips 56 into hole 72, tips 56 may be somewhat close together due to being at least partially converged, and proximal end 64 of graft vessel 60 may be compressed. As previously discussed herein, in one embodiment tips 56 may be enclosed by coil element 94 during initial insertion of tips 56 into hole 72. Tips 56 are positioned in hole 72 such that lower surface 28 of base 20 opposes receiving vessel 70. The axial spacing between lower surface 28 of base 20 and receiving vessel 70 may be provided by angled segments 55 of arms 52 to ensure that proximal end 64 of graft vessel 60 contacts vessel wall 71 of receiving vessel 70 before base 20 contacts vessel wall 71. During the procedure, the surgeon or assistant may apply slight pressure to body section 12, in which case arms 52 may flex and allow lower surface 28 of base 20 to contact vessel wall 71. However, the procedure could be performed without lower surface 28 ever contacting vessel wall 71.

As shown in a top plan view in FIG. 8E, once tips 56 are inserted into hole 72, cam 40 may then be manually rotated in a clockwise direction such that arms 52 retract toward an expanded position, thereby expanding graft vessel 60, such that tips 56 engage a portion of vessel wall 71. If coil element 94 was applied to tips 56, then cam 40 may be manually rotated in a clockwise direction, such that when the coil element 94 is removed, arms 52 are allowed to freely spring back toward an expanded position. However, if coil element 94 was not used, then cam 40 may be manually rotated in a clockwise direction allowing arms 52 to gradually retract toward an expanded position. The diameter of hole 72 may dictate how far arms 52 are allowed to retract and thus, how far tips 56 are expanded. Once cam 40 is rotated and tips 56 engage vessel wall 71, handles 42 may be spaced from clockwise-oriented stops 25 of their respective horizontally-oriented elongated openings 16 if arms 52 are not in the fully expanded position. However, cam 40 may nevertheless be rotated completely until handles 42 engage clockwise-oriented stops 25 of their respective horizontally-oriented elongated openings 16. In one embodiment this may be desirable because arms 52 apply a resistive force against vessel wall 71 when hole 72 is sized to be smaller than the circle defined by arms 52 in the fully expanded position and smaller than proximal end 64 of graft vessel 60. The resistive force helps to stabilize vessel holding device 10 such that proximal end 64 of graft vessel 60 remains steady while the surgeon attaches it to proximal receiving vessel 70.

As shown in FIG. 8F, once graft vessel 60 is suitably positioned, a lip 63 forms a seal around hole 72 on vessel wall 71 and vessel perfusion will occur. Thus, vessel holding device 10 could hold graft vessel 60 open over hole 72 in a hemostatic fashion, while allowing blood to flow into graft vessel 60. Once the seal is formed, the surgeon may attach graft vessel 60 to receiving vessel 70 as blood is flowing through graft vessel 60. Suturing device 68 is shown providing sutures to proximal end 64 of graft vessel 60 and vessel wall 70 in FIGS. 8E & 8F. In FIG. 8E, a needle of suturing device 68 penetrates the lip 63 of the graft vessel 60 and the underlying vessel wall 71 of the receiving vessel 70. Sutures may then connect the graft vessel 60 and the receiving vessel 70.

Figure 8G:
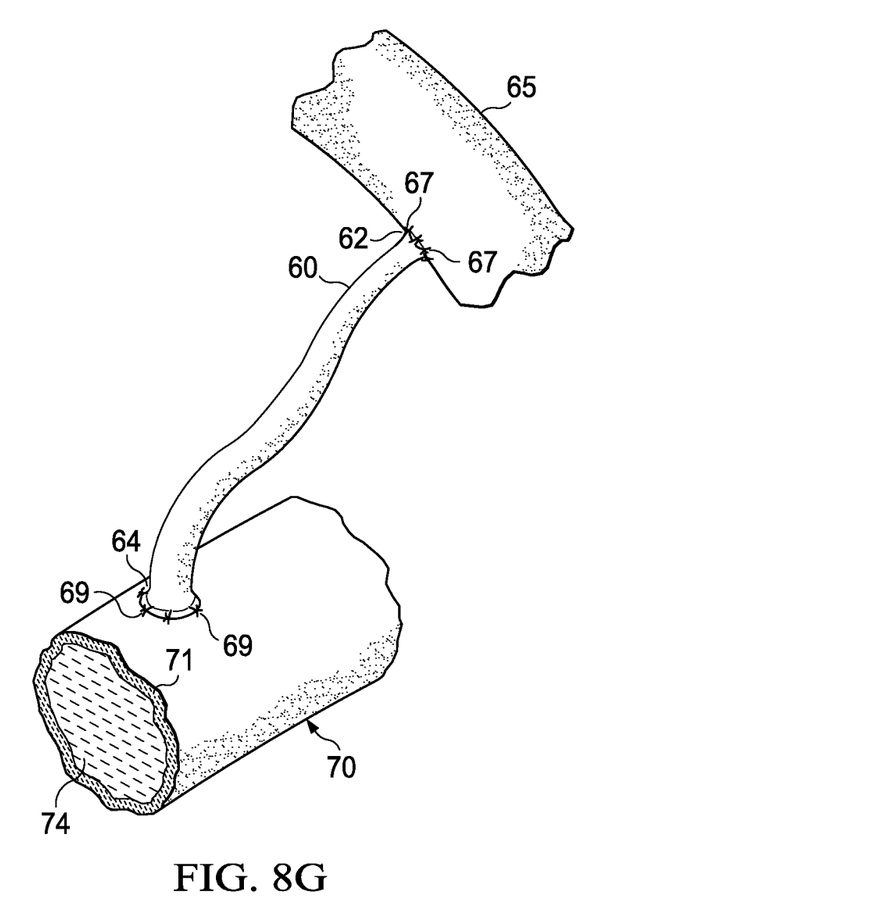
FIG. 8G is a side view of proximal and distal receiving vessels of FIG. 8F shown sutured to the graft vessel after the vessel holding device has been removed in accordance with one example operation in the present disclosure.

As shown in FIGS. 8E & 8F, suturing may be performed through open area 14 of vessel holding device 10. Open area 14 provides an unobstructed view and direct access to the surgical site. Alternatively, a clip or some other mechanism may be used to join graft vessel 60 to vessel wall 71. However, sutures may be desirable because they offer a customary and effective protocol for the surgeon. FIG. 8G illustrates a series of sutures 69 having been properly placed at proximal end 64 of graft vessel 60. The design of vessel holding device 10 with open area 14 allows the surgeon to easily apply either an uninterrupted suture or interrupted sutures, as desired, to create the proximal anastomosis. In addition, the surgeon is not limited to purse string sutures, but may choose the most advantageous type for the given situation.

Note that any of the previously discussed materials could be included in a given kit, which could ostensibly be provided to a physician who is responsible for performing a procedure. A basic kit could include, for example, a given vessel holding device 10 and coil element 94. The kit could also include one or more closures for suturing or affixing the graft vessel. Any of these components may be manufactured based on particular specifications or specific patient needs. The present disclosure contemplates considerable flexibility in such components, as any permutation or modification to any of these elements is clearly within the broad scope of the present disclosure.

It is important to note that the stages and steps in the preceding FIGURES illustrate only some of the possible situations that may be executed by, or within, the designs of the present disclosure. Some of these stages and/or steps may be deleted or removed where appropriate, or these stages and/or steps may be modified or changed considerably without departing from the scope of the present disclosure. In addition, the timing of these operations may be altered considerably. For example, as previously noted, the design of vessel delivery device 10 permits the surgeon to determine the order in which to accomplish proximal and distal anastomosis. Thus, the preceding example flows have been offered for purposes of teaching and discussion. Substantial flexibility is provided by the disclosed architecture in that any suitable arrangements, chronologies, configurations, and timing mechanisms may be provided without departing from the broad scope of this present disclosure.

Note also that the example embodiments described above can be replaced with a number of potential alternatives where appropriate. The processes and configurations discussed herein only offer some of the numerous potential applications of vessel holding device 10. The elements and operations listed in FIGS. 1-8 may be achieved with the use of vessel holding device 10 in any number of contexts and applications. Accordingly, suitable infrastructure may be included within a given system or may cooperate with vessel holding device 10 to effectuate the tasks and operations of the elements and activities associated with managing a procedure.

Although the present disclosure references particular embodiments in FIGS. 1-8, it should be understood that various other changes, substitutions, and alterations may be made hereto without departing from the sphere and scope of the present disclosure. For example, although the preceding FIGURES have referenced a number of components as participating in the numerous outlined procedures, any suitable equipment or relevant tools may be readily substituted for such elements and, similarly, benefit from the teachings of the present disclosure. These may be identified on a case-by-case basis, whereby a certain patient may present a health risk factor while another (with the same condition) may not. Hence, the present tool may be designed based on particular needs with particular scenarios envisioned.

It is also imperative to note that although the present disclosure implicates several example procedures, this has only been done for purposes of example. Vessel holding device 10 could readily be used in virtually any procedure where it would be beneficial and, accordingly, should be construed as such. Vessel holding device 10 may easily be used to provide a viable vascular management solution at various locations of the mammalian anatomy, which are not necessarily illustrated by the preceding FIGURES.

Numerous other changes, substitutions, variations, alterations, and modifications may be ascertained to one skilled in the art and it is intended that the present disclosure encompass all such changes, substitutions, variations, alterations, and modifications as falling within the spirit and scope of the appended claims.

What is claimed is:

1. An apparatus, comprising:
   a body section including an upper surface, a lower surface, and an inner edge disposed around at least a portion of an open area; and
   a plurality of arms each having an exposed portion extending from the body section into the open area, each of the exposed portions including a segment connected to a tip portion, wherein the tip portions are vertically aligned relative to the body section, wherein the tip portions are in opposing relation and are configured to hold a graft vessel, wherein the segments are angled outwardly from respective tip portions toward the body section, wherein the exposed portions of the plurality of arms are radially retractable relative to the body section to cause the opposing tip portions to retract to an expanded position, wherein the tip portions maintain the same vertical alignment relative to the body section as the tip portions retract to the expanded position, wherein the lower surface of the body section opposes a receiving vessel when the opposing tip portions are positioned to transfer the graft vessel to the receiving vessel, such that an end of the graft vessel is axially accessible through the open area when the opposing tip portions are in the expanded position.

2. The apparatus of claim 1, wherein the body section includes a first end opposing a second end, the first and second ends defining a gap sized to permit the graft vessel to pass therethrough.

3. The apparatus of claim 1, wherein the plurality of arms are axially spaced from the upper surface of the body section.

4. The apparatus of claim 1, wherein the opposing tip portions are axially spaced from the lower surface of the body section.

5. The apparatus of claim 1, wherein the body section further comprises:
   a base; and
   a cam operably connected to the base and adapted to move relative to the base, wherein the cam is configured to engage the plurality of arms such that at least a portion of each of the plurality of arms extends radially inward from the body section during movement of the cam in one direction and retracts radially outward into the body section during movement of the cam in an opposite direction.

6. The apparatus of claim 5, wherein the movement of the cam is a rotational movement.

7. The apparatus of claim 5, wherein each of the plurality of arms is made of nickel titanium, and wherein the movement of the cam in at least one of the directions is caused by a force being applied to the cam.

8. The apparatus of claim 1, wherein the plurality of arms are extendable from the body section to cause the opposing tip portions to converge to a converged position.

9. The apparatus of claim 1, wherein the lower surface of the body section is axially spaced from the receiving vessel when the opposing tip portions are positioned to transfer the graft vessel to the receiving vessel.

10. An apparatus, comprising:
    a body section including an upper surface, a lower surface, and an inner edge disposed around at least a portion of an open area; and
    a plurality of arms including exposed portions extending from the body section into the open area, the exposed portions including opposing tip portions configured to hold a graft vessel, wherein the exposed portions are radially extendable and retractable relative to the body section, wherein the opposing tip portions are movable between an expanded position when the exposed portions are retracted and a converged position when the exposed portions are extended, wherein the opposing tip portions are configured in vertical alignment relative to the body section and maintain the same vertical alignment relative to the body section when moving between the expanded and converged positions, wherein the opposing tip portions are spaced from the inner edge when the opposing tip portions are fully expanded, wherein the lower surface of the body section opposes a receiving vessel when the opposing tip portions are positioned to transfer the graft vessel to the receiving vessel, such that an end of the graft vessel is axially accessible through the open area when the opposing tip portions are fully expanded.

11. The apparatus of claim 10, wherein the body section further comprises:
    a base; and
    a cam operably connected to the base and adapted to move relative to the base, wherein the cam is configured to engage the plurality of arms such that the exposed portion of each of the plurality of arms extends from the body section during movement of the cam in one direction and retracts toward the body section during movement of the cam in an opposite direction.

12. The apparatus of claim 10, wherein the lower surface of the body section is axially spaced from the receiving vessel when the opposing tip portions are positioned to transfer the graft vessel to the receiving vessel.

13. The apparatus of claim 10, wherein the body section includes a first end opposing a second end, the first and second ends defining a gap sized to permit the graft vessel to pass therethrough.

* * * * *